United States Patent [19]
Kao

[11] Patent Number: 5,927,884
[45] Date of Patent: Jul. 27, 1999

[54] DISPOSABLE PERFUME STICK

[76] Inventor: Yu-Chien Kao, 2, Alley a, La. 29, Sec. 2, Pei-Shin Rd., Shin-Tien, Taiwan

[21] Appl. No.: 09/014,582

[22] Filed: Jan. 28, 1998

[51] Int. Cl.[6] .......................... A45D 34/04; A61F 13/40; A61M 35/00
[52] U.S. Cl. ...................... 401/132; 132/318; 222/187; 401/156; 401/196; 604/3
[58] Field of Search ................................. 401/132–135, 401/156, 196; 604/3; 222/187; 132/318, 317

[56] References Cited

U.S. PATENT DOCUMENTS

| | | | |
|---|---|---|---|
| 1,332,859 | 3/1920 | Sweet | 604/3 |
| 3,614,245 | 10/1971 | Schwartzman | 401/132 |
| 4,415,288 | 11/1983 | Gordon et al. | 401/132 |
| 4,875,602 | 10/1989 | Chickering et al. | 222/187 |

Primary Examiner—Henry J. Recla
Assistant Examiner—Kathleen J. Prunner
Attorney, Agent, or Firm—Bacon & Thomas

[57] ABSTRACT

A perfume stick having a fragile core tube holding a liquid perfume and mounted in a flexible plastic outer tube, the flexible plastic outer tube having a bottom end covered with a cotton tip, the liquid perfume flowing out of the core tube to the cotton tip for application when the perfume stick is bent by hand to break the core tube.

11 Claims, 4 Drawing Sheets

DISPOSABLE PERFUME STICK

BACKGROUND OF THE INVENTION (a) Field of the Invention

The present invention relates to a perfume stick, and more particularly to a disposable perfume stick for personal use.

(b) Description of the Prior Art

In order to provide a good smell, women usually apply a perfume to the body before going outdoors. Because the good smell of a liquid perfume cannot last for long after its application to the body, a woman may have to apply a perfume to the body several times a day. Further, regular perfumes are commonly made in a liquid state and packed in a container or perfume stick. Because a perfume container or perfume stick holds a certain volume of perfume which is volatile, contained perfume changes into vapor quickly when the perfume container or perfume stick is frequently opened and then closed.

SUMMARY OF THE INVENTION

It is one object of the present invention to provide a disposable perfume stick which can be conveniently carried in the pocket for personal use. It is another object of the present invention to provide a disposable perfume stick which is sealed from the air before use. To achieve these and other objects of the present invention, there is provided a perfume stick which comprises a fragile core tube holding a liquid perfume and mounted in a flexible plastic outer tube. The flexible plastic outer tube has a bottom end covered with a cotton tip. The liquid perfume flows out of the core tube to the cotton tip for application when the perfume stick is bent by hand to break the core tube.

DETAILED DESCRIPTION OF THE PREFERRED EMBODIMENT

Figure 1:
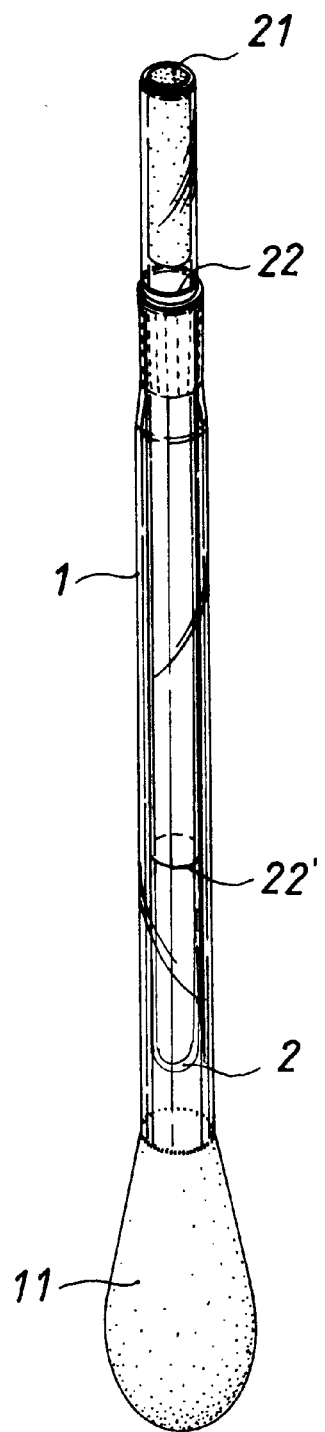
FIG. 1 is a perspective view of a disposable perfume stick according to the present invention.
Figure 2:
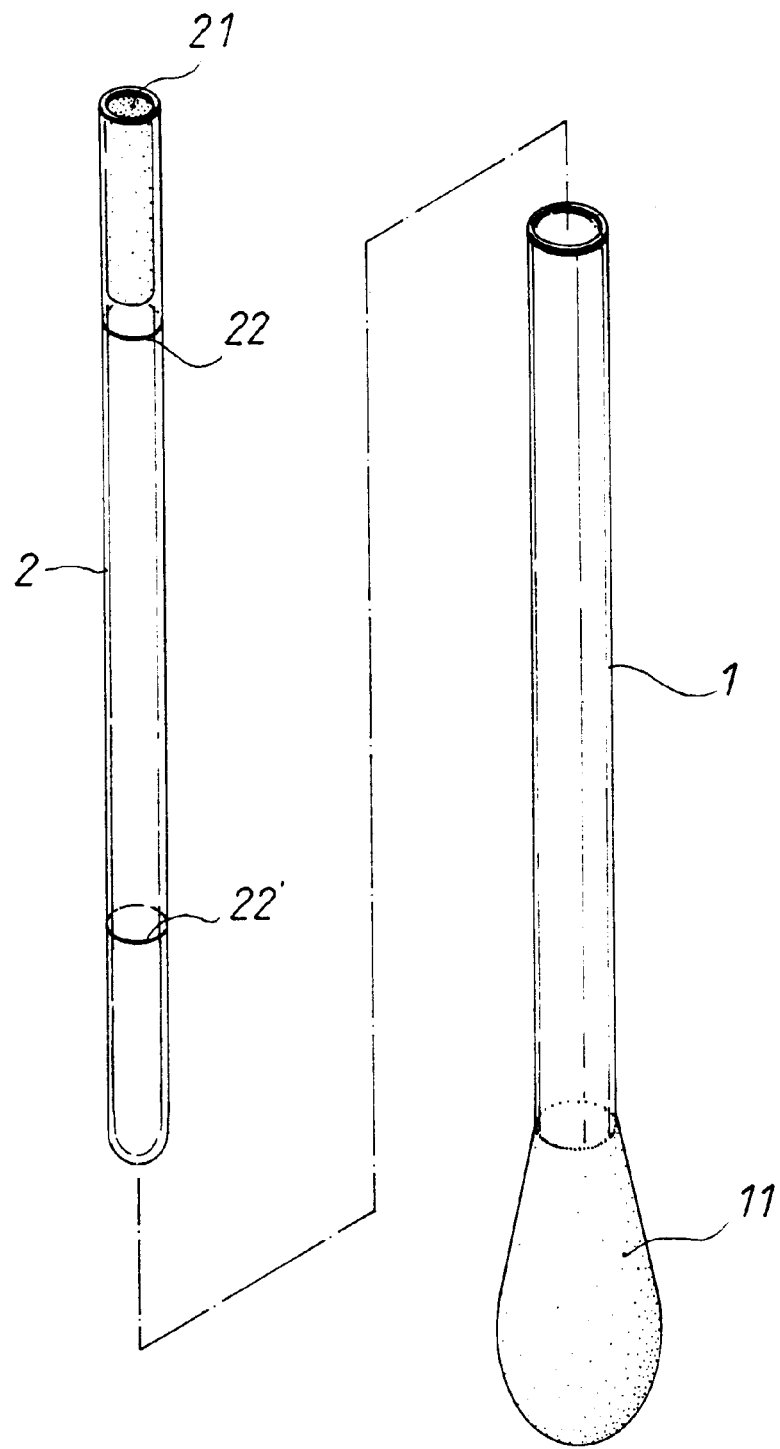
FIG. 2 is an exploded view of the disposable perfume stick shown in FIG. 1.

Referring to FIGS. 1 and 2, a disposable perfume stick in accordance with the present invention is comprised of an outer tube 1, and a core tube 2 mounted in the outer tube 1.

Figure 3:
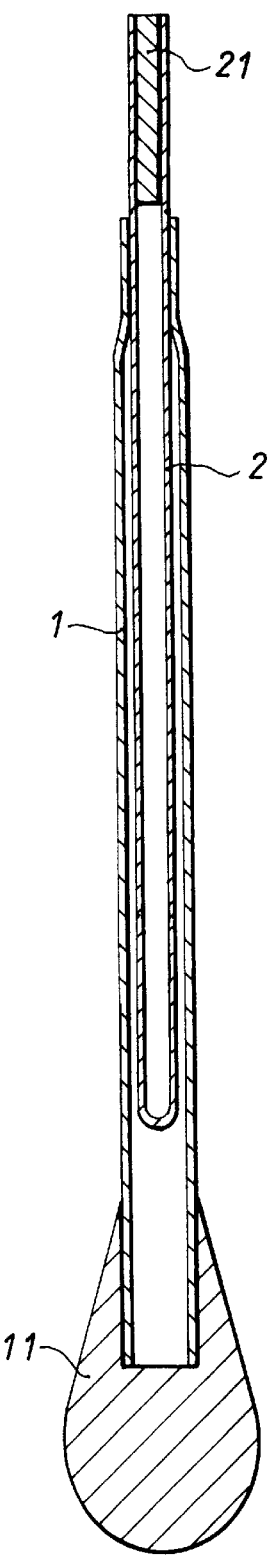
FIG. 3 is longitudinal view in section of the disposable perfume stick shown in FIG. 1.
Figure 4:
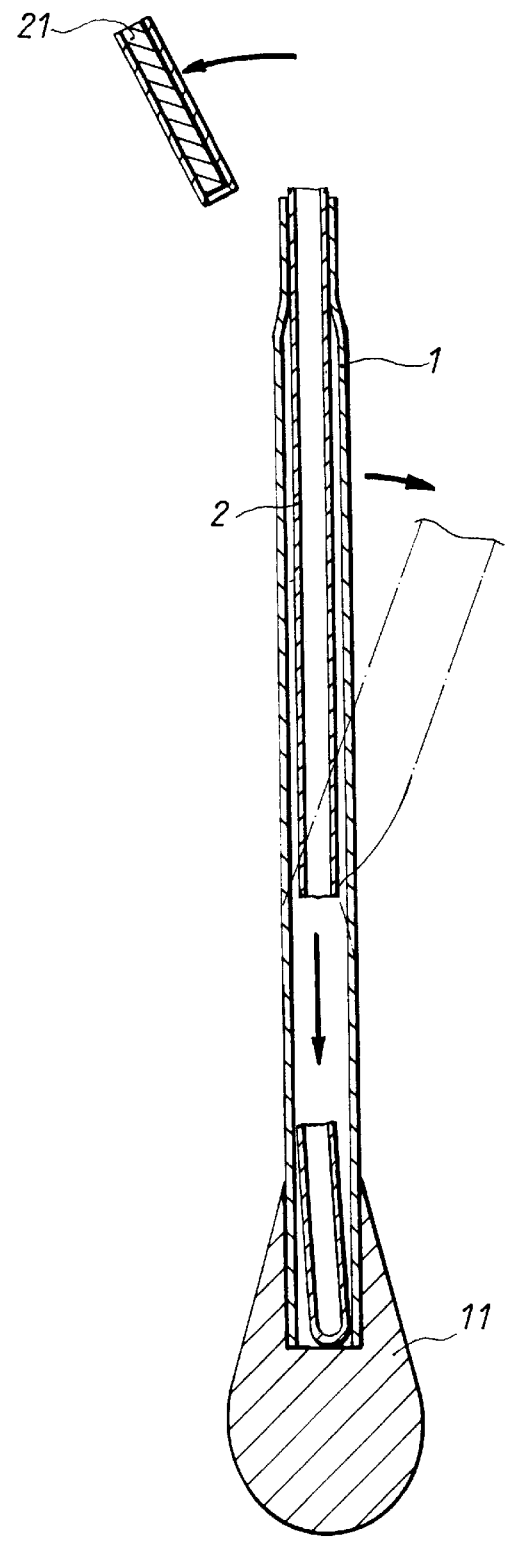
FIG. 4 is an applied view of the present invention, showing the core tube broken.

Referring to FIGS. 3 and 4 and FIGS. 1 and 2 again, the outer tube 1 is a flexible plastic tube having an open top end, an open bottom one, and a cotton tip 11 covered on the open bottom end. The core tube 2 is made from fragile material such as acrylic, having an open end and a close end. After a liquid perfume is filled in the core tube 2, the open end of the core tube 2 is sealed with a silicon rubber stopper 21. Alternatively, alcohol or medical oil may also be filled in the core tube. Further, the core tube 2 has an upper annular frangible dented portion 22 and a lower annular frangible portion 22' near its both ends. The upper annular frangible portion 22 is disposed adjacent to the bottom side of the silicon rubber stopper 21. When the core tube 2 is inserted through the open top end into the inside of the outer tube 1, the upper annular frangible portion 22 of the core tube 2 is disposed above the topmost edge of the outer tube 1, then the top end of the outer tube 1 is sealed to the periphery of the core tube 2 by thermal welding. When in use, the outer tube 1 is bent by hand to break the core tube 2 at the lower annular frangible portion 22', then top end of the core tube 2 is broken along the upper annular frangible portion 22, permitting atmospheric pressure to pass into the core tube 2 and to force contained liquid perfume out of the broken bottom end of the core tube 2 to the cotton tip 11 for application. After the perfume stick has served its purpose, it is thrown away.

Figure 5:
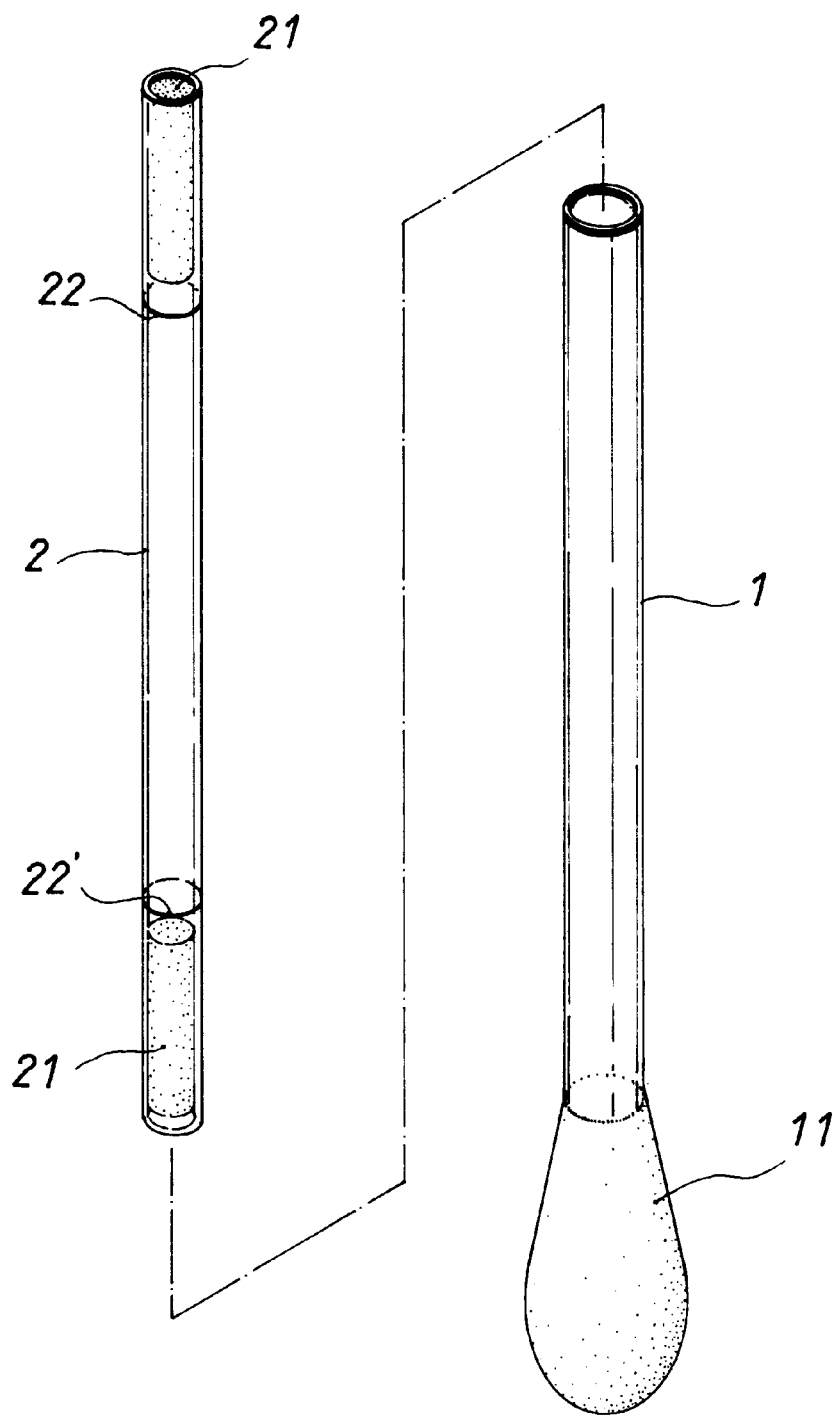
FIG. 5 is an exploded view of an alternate form of the disposable perfume stick according to the present invention.

FIG. 5 shows an alternate form of the present invention, in which the core tube 2 is a double open tube having both open ends sealed with a respective silicon rubber stopper 21, and two annular frangible portions 22;22' spaced around the periphery near the top and bottom ends thereof adjacent to the silicon rubber stoppers 21.

It is to be understood that the drawings are designed for purposes of illustration only, and are not intended as a definition of the limits and scope of the invention disclosed.

What the invention claimed is:

1. A perfume stick comprising an outer tube, and a core tube holding a liquid and mounted in said outer tube, wherein said outer tube is made from flexible plastics, having an open top end, an open bottom end, and a cotton tip covered on the open bottom end; said core tube having sidewalls made from fragile material and inserted through the open top end into the inside of said outer tube, said core tube having a closed bottom end and an open top end sealed with sealing means and extended out of said outer tube, whereby said core tube can be fractured by bending the outer tube.

2. The perfume stick of claim 1, wherein said core tube is molded from acrylic resin.

3. The perfume stick of claim 1, wherein said sealing means is a silicon rubber stopper.

4. The perfume stick of claim 1, wherein said core tube has an upper annular frangible portion and a lower annular frangible portion near two opposite ends thereof.

5. The perfume stick of claim 4, wherein said upper frangible portion is disposed below said sealing means.

6. The perfume stick of claim 4, wherein said core tube has an open bottom end sealed with a silicon rubber stopper.

7. The perfume stick of claim 6, wherein the silicon rubber stopper at the open bottom end of said core tube is disposed below said lower annular frangible portion.

8. The perfume stick of claim 1, wherein said liquid is alcohol.

9. The perfume stick of claim 1, wherein said liquid is a perfume.

10. The perfume stick of claim 1, wherein said liquid is a medical oil.

11. The perfume stick of claim 1, wherein the open top end of said outer tube is sealed to the periphery of said core tube by thermal welding.

* * * * *